US006886566B2

(12) United States Patent
Eubank

(10) Patent No.: US 6,886,566 B2
(45) Date of Patent: May 3, 2005

(54) ORAL APPLIANCE FOR MAINTAINING STABILITY OF ONE OR MORE ASPECTS OF A USER'S MASTICATORY SYSTEM

(76) Inventor: Jimmy B. Eubank, 1401 Chatsworth La., Plano, TX (US) 75075

( * ) Notice: Subject to any disclaimer, the term of this patent is extended or adjusted under 35 U.S.C. 154(b) by 0 days.

(21) Appl. No.: 10/193,392

(22) Filed: Jul. 11, 2002

(65) Prior Publication Data

US 2004/0007237 A1 Jan. 15, 2004

(51) Int. Cl.$^7$ ............................................. A61C 5/14
(52) U.S. Cl. ........................ 128/859; 128/860; 128/861
(58) Field of Search .............................. 128/846, 848, 128/859–862; 602/902; 433/6

(56) References Cited

U.S. PATENT DOCUMENTS

| | | | | |
|---|---|---|---|---|
| 5,868,138 | A | * | 2/1999 | Halstrom .................... 128/859 |
| 6,055,986 | A | * | 5/2000 | Meade ........................ 128/848 |
| 6,505,625 | B1 | * | 1/2003 | Uenishi ...................... 602/702 |
| 6,530,375 | B1 | | 3/2003 | Cieslik, Jr. .................. 128/848 |

FOREIGN PATENT DOCUMENTS

| | | | |
|---|---|---|---|
| CA | 2208624 | 1/1999 | ............ A61C/5/14 |
| EP | 1205157 A1 | 5/2002 | ............ A61C/7/08 |
| GB | 172079 | 11/1921 | |

OTHER PUBLICATIONS

PCT, Notification of Transmittal of the International Search Report or the Declaration, International Application No. PCT/US03/21057, 8 pages, Feb. 11, 2004.

(Continued)

*Primary Examiner*—Michael Brown
(74) *Attorney, Agent, or Firm*—Baker Botts L.L.P.

(57) ABSTRACT

In one embodiment, an oral appliance includes a first arch adapted to receive at least some of a user's teeth and a second arch adapted to receive at least some of the user's teeth. The first arch includes an anterior substantially planar region, a right posterior substantially planar region, and a left posterior substantially planar region. The second arch includes an anterior bearing point, a right posterior bearing point, and a left posterior bearing point. Each bearing point of the second arch contacts a corresponding substantially planar region of the first arch when the user bites down with the oral appliance inserted in the user's mouth and the user's temporomandibular joint in its proper natural position. In a more particular embodiment, the oral appliance may be used to help maintain stability of one or more aspects of the user's masticatory system, including at least helping to maintain proper positioning of the user's temporomandibular joint.

39 Claims, 4 Drawing Sheets

OTHER PUBLICATIONS

A. Sheikholeslam and C. Riise, "Influence of experimental interfering occlusal contacts on the activity of the anterior temporal and masseter muscles during submaximal and maximal bite in the intercuspal position," Journal of Oral Rehabilitation, vol. 10, pp. 207–214, Manuscript dated, Jul. 3, 1981.

E.H. Williamson, and D.O. Lundquist,"Anterior guidance: Its effect on electromyographic activity of the temporal and masseter muscles," The Journal of Prosthetic Dentistry, vol. 49, No. 6, 8 pages, Jun. 1983.

P.E. Mahan, et al., "Superior and inferior bellies of the lateral pterygoid muscle EMG activity at basic jaw positions," Research and Education, vol. 50, No. 5, 9 pages, Nov. 1983.

PCT, International Searching Authority, 4 pages, Oct. 21, 2003.

Robert M. Morrow, "Centric Check–Point Procedure for Determining the Accuracy of Jaw Relation Records," Overdentures, Chapter 16, 6 pages, 1975©.

Catalog, "Dawson Deprogrammer Splint" device, Great Lakes Orthodontics, Ltd. catalog page, 1 page. 1996.

Catalog, close–up photo of "Dawson Deprogrammer Splint" device, Great Lakes Orthodontics, Ltd. catalog page, 1 page. 1996.

* cited by examiner

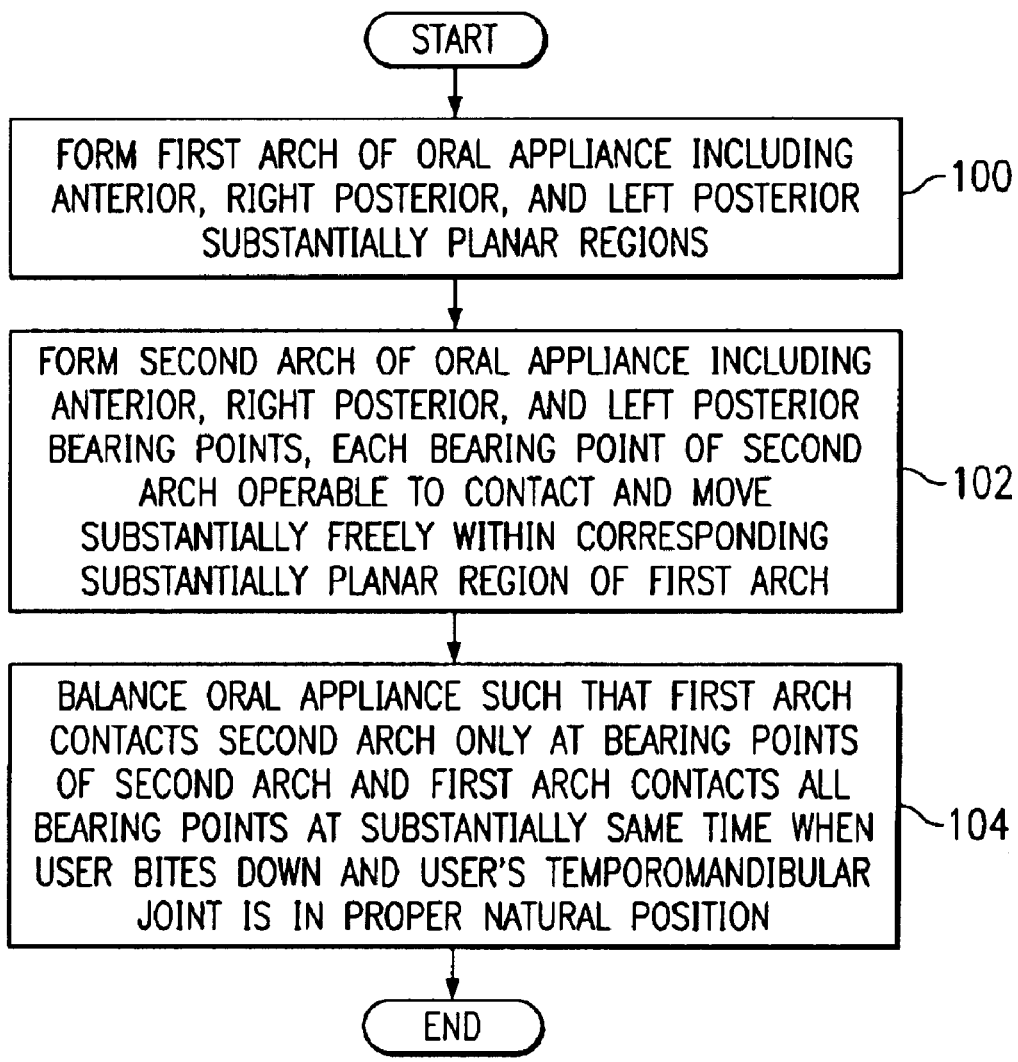

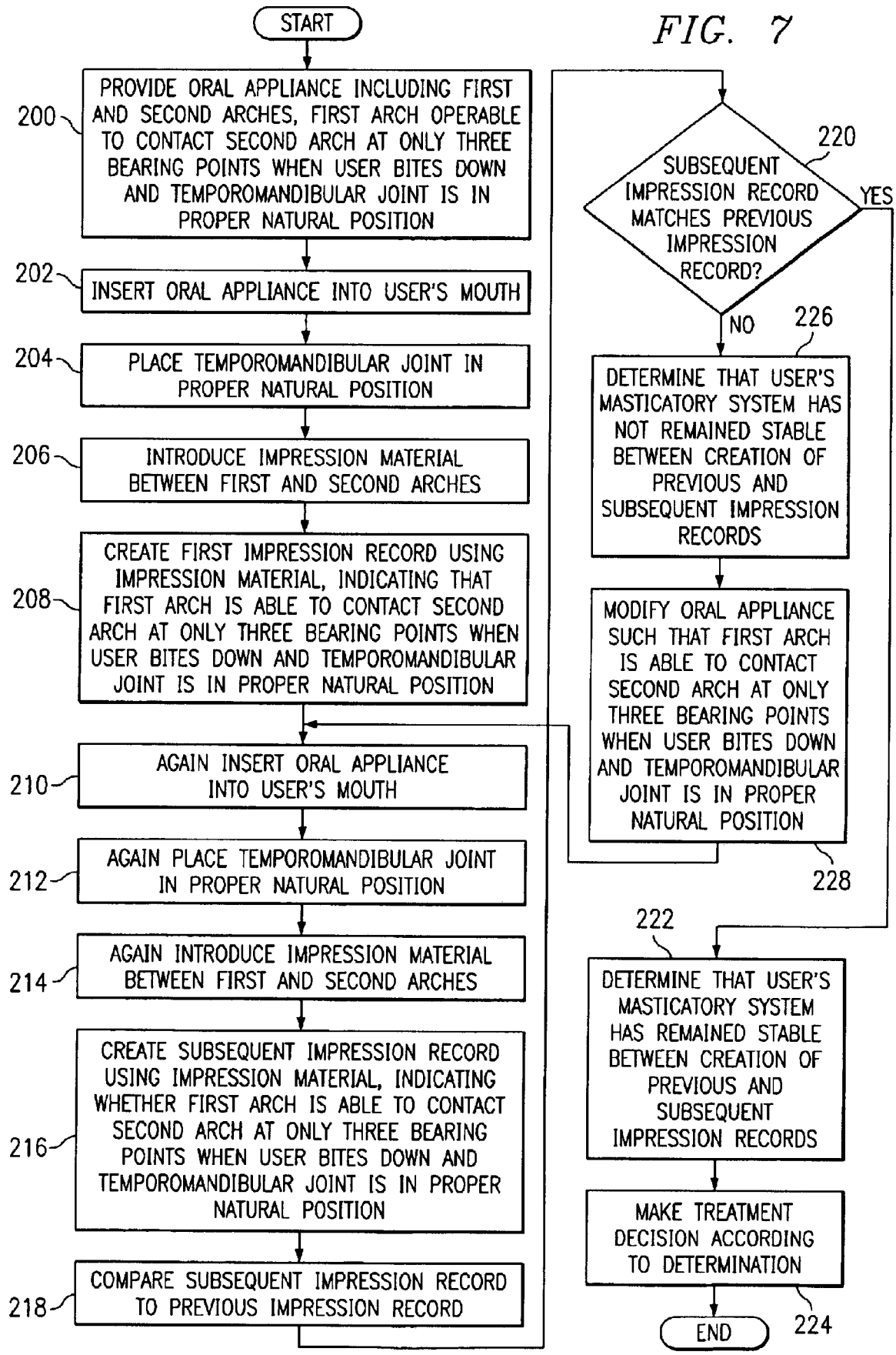

ORAL APPLIANCE FOR MAINTAINING STABILITY OF ONE OR MORE ASPECTS OF A USER'S MASTICATORY SYSTEM

TECHNICAL FIELD OF THE INVENTION

This invention relates generally to oral appliances and in particular to an oral appliance for maintaining stability of one or more aspects of a user's masticatory system.

BACKGROUND OF THE INVENTION

Many people experience problems resulting from improper positioning of the temporomandibular joint and associated musculature. For example, grinding of teeth during sleep, a very common condition resulting from improper positioning of the joint and associated musculature, may lead to excessive wear of teeth, loose teeth, rotation or migration of teeth, cracked or broken teeth, headaches, pain or tenderness of the joint and associated musculature, popping or clicking of the joint, deterioration of the joint, or other problems associated with the masticatory system. As dental technology advances and people demand more effective treatment options, reducing or eliminating such problems becomes increasingly important.

Previous oral appliances for treating such problems include a single upper or lower arch customized to conform to a user's upper or lower teeth, respectively. In use, the single arch prevents the user's upper and lower teeth from grinding against one another during sleep. Although such oral appliances reduce or eliminate certain symptoms of grinding (e.g., excessive wear of the teeth), they typically do very little if anything to address the underlying physiological cause—improper positioning of the temporomandibular joint and associated musculature—and may even exacerbate the situation in some cases. Furthermore, natural physiological triggers based on the manner in which forces are applied to the teeth may affect the joint and associated musculature such that problems, such as deterioration of the joint, continue despite use of such oral appliances.

These effects may be minimized if oral appliances are carefully constructed such that all the opposing lower (or upper) teeth contact the upper (or lower) arch at the same time when the user bites down. However, this is often difficult and time-consuming even for highly skilled dentists or other clinical professionals. Moreover, the positions of the opposing lower (or upper) teeth may continue to shift in response to repeatedly contacting the upper (or lower) arch when the user bites down, which may necessitate adjustment or re-construction of the oral appliance such that all the opposing lower (or upper) teeth again contact the upper (or lower) arch at the same time when the user bites down. As this cycle perpetuates, additional instability and deterioration of the user's masticatory system may occur.

These and other deficiencies have made previous oral appliances inadequate for the needs of many users.

SUMMARY OF THE INVENTION

The oral appliance of the present invention may reduce or eliminate problems and disadvantages associated with previous oral appliances.

According to one embodiment of the present invention, an oral appliance includes a first arch adapted to receive at least some of a user's teeth and a second arch adapted to receive at least some of the user's teeth. The first arch includes an anterior substantially planar region, a right posterior substantially planar region, and a left posterior substantially planar region. The second arch includes an anterior bearing point, a right posterior bearing point, and a left posterior bearing point. Each bearing point of the second arch is operable to contact a corresponding substantially planar region of the first arch when the user bites down with the oral appliance inserted in the user's mouth and the user's temporomandibular joint in its proper natural position. In a more particular embodiment, the oral appliance may help maintain stability of one or more aspects of the user's masticatory system, at least helping to maintain proper positioning of the user's temporomandibular joint.

According to another embodiment, a method of constructing an oral appliance includes forming a first arch adapted to receive at least some of a user's teeth, the first arch comprising an anterior substantially planar region, a right posterior substantially planar region, and a left posterior substantially planar region. The method further includes forming a second arch adapted to receive at least some of the user's teeth, the second arch comprising an anterior bearing point, a right posterior bearing point, and a left posterior bearing point. Each bearing point of the second arch is operable to contact a corresponding substantially planar region of the first arch when the user bites down with the oral appliance inserted in the user's mouth and the user's temporomandibular joint in its proper natural position. The constructed oral appliance includes the first and second arches.

According to another embodiment, a method of monitoring stability of one or more aspects of a user's masticatory system includes providing an oral appliance including a first arch and a second arch each adapted to receive at least some of the user's teeth, the first arch operable to contact the second arch at only three bearing points when the user bites down with the oral appliance inserted in the user's mouth and the user's temporomandibular joint in its proper natural position. The oral appliance is inserted into the user's mouth and an impression material is introduced between the first and second arches. A first impression record is created using the impression material, indicating that the first arch is operable to contact the second arch at only the three bearing points when the user bites down with the oral appliance inserted in the user's mouth and the user's temporomandibular joint in its proper natural position. At a subsequent time, the oral appliance is again inserted into the user's mouth and an impression material is again introduced between the first and second arches. A second impression record is created using the impression material, indicating whether the first arch is operable to contact the second arch at only the three bearing points when the user bites down with the oral appliance inserted in the user's mouth and the user's temporomandibular joint in its proper natural position. The second impression record is compared to the first impression record. If the second impression record matches the first impression record, it may be determined that one or more aspects of the user's masticatory system have remained stable over a period of time between creation of the first and second impression records.

Particular embodiments of the present invention may provide one or more technical advantages. For example, in particular embodiments, an oral appliance is provided with upper and lower arches that may be constructed and "balanced" such that a first arch contacts a second arch only at three bearing points, and such that the first arch contacts these bearing points at substantially the same time, when the user bites down and the user's temporomandibular joint is in its proper natural position. When the oral appliance is in use, the three bearing points may be permitted to move substantially freely within corresponding substantially planar regions. However, in particular embodiments, due to the natural movement of the user's lower jaw about the joint, only the anterior bearing point remains in contact with its corresponding substantially planar region when the user is not biting down and the lower jaw is retracted. In particular embodiments, the anterior bearing point is formed such that it remains in contact with its corresponding substantially planar region regardless of positioning or movement of the lower jaw. Because it ensures that the joint is in its proper natural position when the user bites down, particular embodiments may not only reduce or eliminate the symptoms of grinding of the teeth (e.g., excessive wear of the teeth), but may further address and remediate the underlying physiological cause—improper positioning of the joint and associated musculature.

In particular embodiments, the present invention may eliminate the difficult and time-consuming task of constructing an oral appliance such that: (1) where two arches are provided, a significant portion of the surface of the upper (or lower) arch substantially simultaneously contacts a significant portion of the opposing surface of the lower (or upper) arch, or (2) where a single arch is provided, the surface of the upper (or lower) arch substantially simultaneously contacts all or most of the user's opposing lower (or upper) teeth. The use of posterior bearing points in addition to an anterior bearing point may reduce the amount of force transferred to the joint when the user bites down to approximately five percent of the force applied, which may be approximately the same as if the entire surfaces of first and second arches contacted each other at the same time. Thus, in particular embodiments, the present invention may provide the same or similar advantages as such an arrangement, while reducing the complexity and time involved in construction. In addition, the use of bearing points and corresponding substantially planar regions may allow the first and second arches to be thinner and more comfortable to wear.

In particular embodiments, a dentist or other clinical professional may monitor the stability of the user's temporomandibular joint, associated musculature, teeth, or one or more other aspects of the user's masticatory system over time according to a series of impression records created using the oral appliance. For example, if the monitoring indicates that the joint has remained sufficiently stable over a period of time between the creation of successive impression records, then the dentist or other clinical professional may be comfortable finalizing the user's case. If not, then the dentist or clinical professional may wish to modify the oral appliance, such as by modifying one or more of the bearing points, to attempt to achieve such stability. In particular embodiments, monitoring may be conducted in connection with the initial fitting and construction of the oral appliance, such as over a period of less than one hour. In particular embodiments, monitoring may be conducted over a longer period, such as over a period of between one week and one year. In particular embodiments, such monitoring may allow a dentist or other clinical professional to make more effective treatment decisions and more accurately predict the likely effects of those decisions.

Certain embodiments may provide all, some, or none of these advantages. Certain embodiments may provide one or more other advantages, one or more of which may be apparent to those skilled in the art from the figures, descriptions, and claims included herein.

BRIEF DESCRIPTION OF THE DRAWINGS

For a more complete understanding of the present invention and advantages thereof, reference is now made to the following description taken in conjunction with the accompanying drawings, in which:

FIG. 6 illustrates an example method of constructing an oral appliance for maintaining stability of one or more aspects of a user's masticatory system; and FIG. 7 illustrates an example method of monitoring stability of one or more aspects of a user's masticatory system using an oral appliance.

DESCRIPTION OF EXAMPLE EMBODIMENTS

Figure 1:
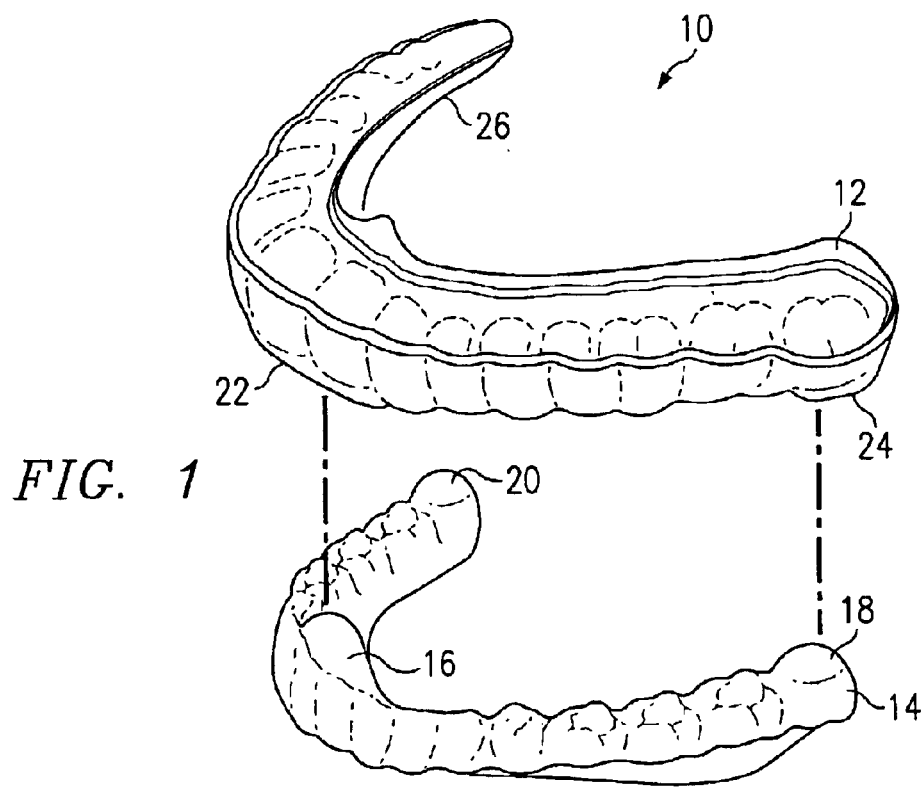
FIG. 1 illustrates a top perspective view of an example oral appliance for maintaining stability of one or more aspects of a user's masticatory system.
Figure 2:
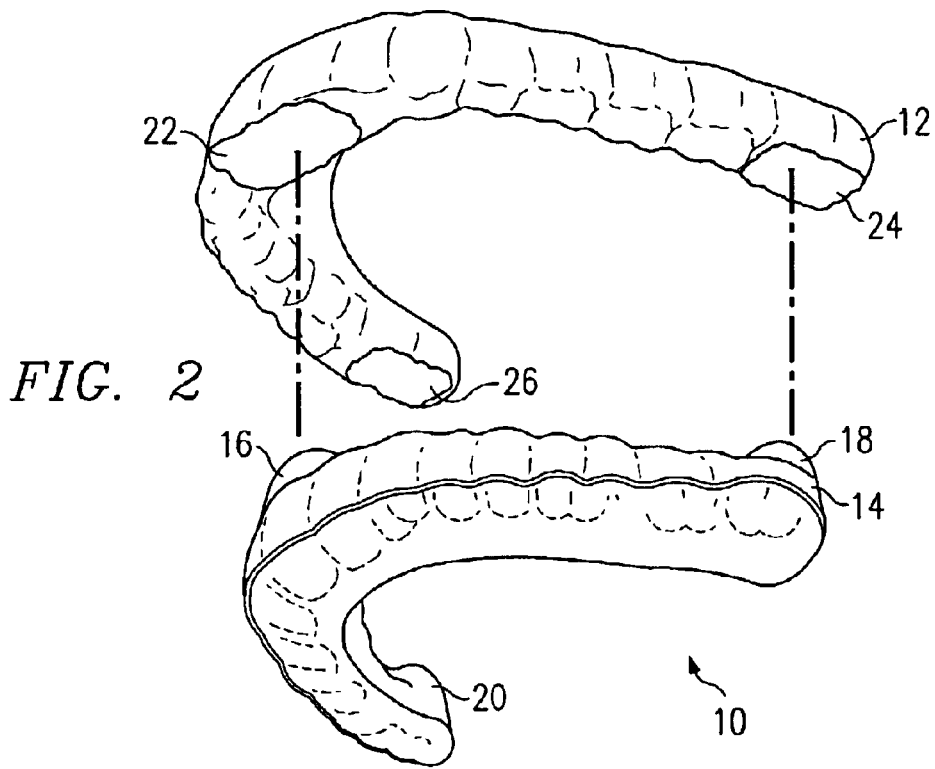
FIG. 2 illustrates a bottom perspective view of an example oral appliance for maintaining stability of one or more aspects of a user's masticatory system.

FIGS. 1 and 2 illustrate top perspective and bottom perspective views, respectively, or an example oral appliance 10 for maintaining stability of one or more aspects of a user's masticatory system. Aspects of the masticatory system include at least the temporomandibular joint, associated musculature, and the teeth, although in certain embodiments of the present invention oral appliance 10 may benefit one or more other aspects of the masticatory system. Oral appliance 10 includes an upper arch 12 adapted to receive at least some of a user's upper teeth and a lower arch 14 adapted to receive at least some of the user's lower teeth. Arches 12 and 14 may be any arches suitable for dental uses. Arches 12 and 14 are preferably high quality custom arches that have been customized to fit the definition of a particular user, for example, from "stone" models using an acrylic, composite, or other material suitable for high quality orthodontic applications. In the alternative, for example, arches 12 and 14 may be formed from a deformable "boil-and-bite" material that is heated to a temperature sufficient to place arches 12 and 14 in a deformable state. Arches 12 and 14 may then be inserted in the user's mouth, conformed to the user's teeth when the user bites down, removed from the user's mouth, and allowed to cool and harden. Although particular examples are described for purposes of illustration, the present invention contemplates arches 12 and 14 being formed in any appropriate manner and using any appropriate material according to particular needs.

Figure 3:
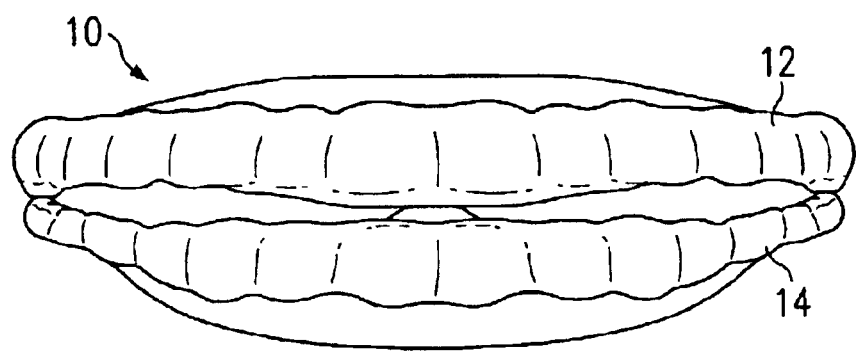
FIG. 3 illustrates a front view of an example oral appliance in which an upper arch contacts a lower arch at only three bearing points.
Figure 4:
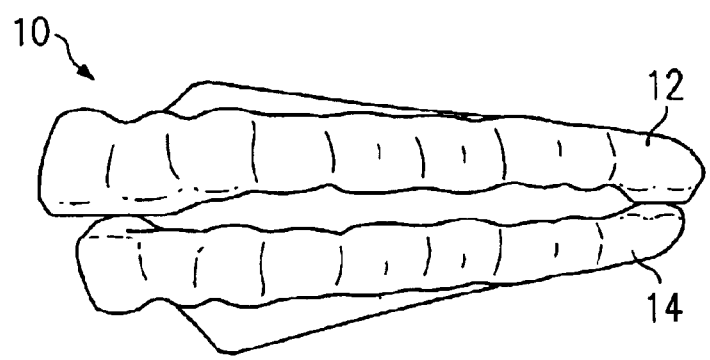
FIG. 4 illustrates a side view of an example oral appliance in which an upper arch contacts a lower arch at only three bearing points.

In one embodiment, lower arch 14 includes at least three bearing points—anterior bearing point 16, right posterior bearing point 18, and left posterior bearing point 20. In this embodiment, upper arch 12 includes at least three corresponding substantially planar regions—anterior substantially planar region 22, right posterior substantially planar region 24, and left posterior substantially planar region 26. As further illustrated in FIGS. 3 and 4, arches 12 and 14 may be constructed and "balanced" such that upper arch 12 contacts lower arch 14 only at bearing points 16, 18, 20, and that upper arch 12 contacts bearing points 16, 18, 20 at substantially the same time, when the user bites down and the user's temporomandibular joint is in its proper natural position.

This is in stark contrast to previous oral appliances which must be carefully constructed to ensure that all the opposing lower (or upper) teeth contact the single upper (or lower) arch at the same time in order to avoid problems, such as further deterioration of a user's temporomandibular joint and associated musculature, despite regular use of the oral appliance, due to natural physiological triggers based on the manner in which forces are applied to the teeth. This is often difficult and time-consuming even for highly skilled dentists or other clinical professionals. In addition, with previous oral appliances the positions of the opposing lower (or upper) teeth may continue to shift in response to repeatedly contacting the upper (or lower) arch when the user bites down, which may necessitate adjustment or re-construction of the oral appliance such that all the opposing lower (or upper) teeth again contact the upper (or lower) arch at the same time when the user bites down. As this cycle perpetuates, additional instability and deterioration of one or more aspects of the user's masticatory system may occur.

When oral appliance 10 is in use, bearing points 16, 18, 20 may be permitted to move substantially freely within the corresponding substantially planar regions 22, 24, 26, respectively. However, due to the natural movement of the user's lower jaw about the joint, typically only anterior bearing point 16 will remain in contact with corresponding substantially planar region 22 when the user is not biting down and, consequently, the lower jaw is retracted. In one embodiment, anterior bearing point 16 is formed such that it remains in contact with corresponding substantially planar region 22 regardless of positioning or movement of the lower jaw. Substantially planar regions 22, 24, 26 may have any suitable dimensions, but preferably are large enough such that the corresponding bearing points 16, 18, 20, respectively, do not slide off of or otherwise move out of substantially planar regions 22, 24, 26 during fitting or use of oral appliance 10.

Although in the described example embodiment bearing points 16, 18, 20 are formed on lower arch 14 and contact upper arch 12 at corresponding substantially planar regions 22, 24, 26, respectively, the present invention contemplates one or more bearing points 16, 18, 20 being formed on upper arch 12 and contacting lower arch 14 at corresponding substantially planar regions 22, 24, 26, respectively. For example, all bearing points 16, 18, 20 may be formed on upper arch 12 and may contact lower arch 14 at substantially planar regions 22, 24, 26, respectively. In addition, although in the described example embodiment three bearing points 16, 18, 20 and corresponding substantially planar regions 22, 24, 26 are provided, the present invention contemplates more or fewer bearing points and corresponding substantially planar regions according to particular needs. As just an example and not by way of limitation, oral appliance 10 could be provided with five bearing points—anterior bearing point 16, forward and rearward right posterior bearing points 18a and 18b, and forward and rearward left posterior bearing points 20a and 20b—along with corresponding substantially planar regions 22, 24a and 24b, and 26a and 26b. The present invention contemplates any oral appliance 10 including an upper arch 12 and a lower arch 14 in which a number of bearing points and corresponding substantially planar regions are provided. This may eliminate the difficult and time-consuming task associated with previous oral appliances of constructing an oral appliance such that the bottom (or top) surface of an upper (or lower) arch, covering all or most of a user's upper (or lower) teeth, must substantially simultaneously contact all or most of the user's lower (or upper) teeth to reduce continuing problems.

Oral appliance 10 could be provided with only anterior bearing point 16 and corresponding substantially planar region 22, without posterior bearing points 18 and 20 and corresponding substantially planar regions 24 and 26, respectively. In this case, as in the case where posterior bearing points 18, 20 and corresponding posterior substantially planar regions 24, 26, respectively, are provided, the substantially free movement of bearing point 16 within corresponding substantially planar region 22 allows the user's temporomandibular joint and associated musculature to alternately retract when the user is not biting down and thereafter return to its proper natural position when the user again bites down. However, it has been determined that the compressive force transferred to the user's joint when the user bites down depends primarily on how far away the nearest point of contact between arches 12 and 14 is from the joint. In particular, if arches 12 and 14 contact one another only at anterior bearing point 16 and corresponding substantially planar region 22, approximately sixty percent of the compressive force applied when the user bites down may be transferred to the joint. This amount of force may be undesirable and may reduce the effectiveness of oral appliance 10 in maintaining the long term health and stability of the joint and other aspects of the masticatory system.

In contrast, when oral appliance 10 further includes posterior bearing points 18, 20 and corresponding substantially planar regions 24, 26, respectively, placed in proximity to the user's most posterior teeth, the compressive force transferred to the joint may be reduced from approximately sixty percent to approximately five percent of the total force applied. The reduction in transferred force may be approximately the same as if the entire bottom surface of upper arch 12 contacted the entire top surface of lower 14 at substantially the same time. Thus, in one embodiment, use of three bearing points 16, 18, 20 and corresponding substantially planar regions 22, 24, 26, respectively, provides the same or similar advantages as such an arrangement, while reducing the complexity and time involved in construction. In addition, use of bearing points 16, 18, 20 and corresponding substantially planar regions 22, 24, 26, respectively, may allow arches 12 and 14 of oral appliance 10 to be thinner and more comfortable to wear than arches associated with previous oral appliances.

In one embodiment, to properly balance oral appliance 10 for the user such that when the user bites down upper arch 12 contacts lower arch only at bearing points 16, 18, 20 and such that upper arch 12 contacts all bearing points 16, 18, 20 at substantially the same time, bearing points 16, 18, 20 are formed on lower arch 14, corresponding substantially planar regions 22, 24, 26 are formed on upper arch 12, and arches 12 and 14 are inserted in the user's mouth. The user is instructed to relax the user's lower jaw to allow the user's temporomandibular joint and associated musculature to retract the user's lower jaw to its proper natural position, this in turn causing bearing points 16, 18, 20 on lower arch 14 to travel rearward within the corresponding substantially planar regions 22, 24, 26, respectively, on upper arch 12. If after the user's lower jaw has been allowed to fully relax for a period of time, ten minutes for example, when the user bites down upper arch 12 contacts lower arch 14 other than at bearing points 16, 18, 20 or upper arch 12 does not contact all bearing points 16, 18, 20 at substantially the same time, then the dentist or other clinical professional balancing oral appliance 10 will then add material, remove material, or otherwise modify one or more bearing points 16, 18, 20 until these conditions are satisfied and proper balancing is achieved.

Once these conditions are satisfied and oral appliance 10 is properly balanced, the user may be instructed to remain in a relaxed state for another period of time, ten minutes for example, after which proper balancing may be verified. For example, during this verification period, positioning of the user's temporomandibular joint and associated musculature may have changed such that the user's lower jaw has further retracted. If when the user bites down after the verification period upper arch 12 still contacts lower arch 14 only at bearing points 16, 18, 20, and upper arch 12 contacts all bearing points 16, 18, 20 at substantially the same time, then proper balancing is verified. Otherwise, the dentist or other clinical professional balancing oral appliance 10 again adds material, removes material, or otherwise modifies one or more bearing points 16, 18, 20 until these conditions are satisfied. One or more such verification periods and associated modifications to bearing points 16, 18, 20 may be needed before the user's temporomandibular joint and associated musculature are stable and proper balancing of oral appliance 20 is achieved. Although modification of bearing points 16, 18, 20 is described, the present invention contemplates the modification of one or more substantially planar regions 22, 24, 26 or any other portion of oral appliance 10 such that conditions for proper balancing are achieved.

Figure 5:
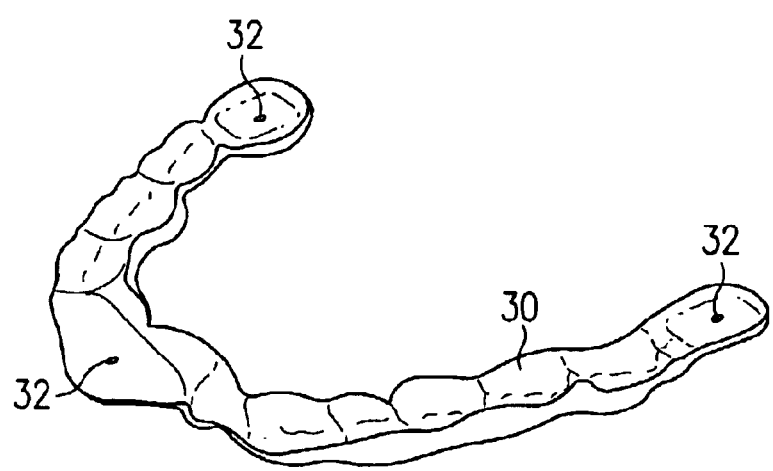
FIG. 5 illustrates an example impression record.

In one embodiment, the dentist or other clinical professional may determine whether, when the user bites down, upper arch 12 contacts lower arch 14 only at bearing points 16, 18, 20 and upper arch 12 contacts all bearing points 16, 18, 20 at substantially the same time using a deformable impression material, such as BLU-MOUSSE for example. The impression material may be placed between arches 12 and 14 after the initial construction and balancing of oral appliance 10 to create a "centric relation" or other impression record 30, such as the example impression record 30 illustrated in FIG. 5. For example, arches 12 and 14 may be inserted in the user's mouth, the user's jaw may be allowed to relax so that the dentist or other clinical professional can physically place the user's temporomandibular joint and associated musculature in its proper natural position, the impression material may be squirted or otherwise introduced into the user's mouth to substantially fill the space between arches 12 and 14, the user may bite down so as to bring arches 12 and 14 in contact through portions of the impression material, the impression material may be allowed to harden, arches 12 and 14 may be removed from the user's mouth, and the impression material may be removed from between arches 12 and 14. If impression record 30 includes a single distinct hole 32 for each bearing point 16, 18, 20, the hole 32 preferably having a distinct border with no residual impression material remaining within the hole 32, then oral appliance 10 may be determined to be properly balanced. If these conditions are not met, then "centric relation" and proper balancing of oral appliance 10 is not achieved and modifications are necessary. Once created, the impression record is preferably archived for later comparison with subsequently created impression records.

In one embodiment, a dentist or other clinical professional may monitor the stability of one or more aspects of the user's masticatory system over time according to a sequence of impression records 30 created using oral appliance 10. If the dentist or clinical professional determines as a result of such monitoring that the monitored aspects of the masticatory system have remained sufficiently stable over a period of time, then the dentist or other clinical professional may be comfortable finalizing the user's case. If not, then the dentist or clinical professional may wish to modify oral appliance 10 such that the monitored aspects of the masticatory system will remain sufficiently stable. As an example, it may be desirable to monitor condylar changes occurring after initially stabilizing a user's occlusion or in users with "at risk" joints. Such monitoring may allow the dentist or other clinical professional to make more effective treatment decisions and more accurately predict the likely effects of those decisions.

For example, a first impression record 30 may be created in connection with initial construction and balancing of oral appliance 10. The user may be instructed to return after some period of time, several weeks for example, so that the balancing of oral appliance 10 can be verified. A second impression record 30 is created and then compared with the first impression record 30. If the second impression record 30 matches the first impression record 30, then the user's masticatory system may be determined to be stable. Armed with this knowledge, the dentist or other clinical professional may finalize the user's case, may proceed with another procedure with comfort that results of the procedure are not likely to be negated due to subsequent changes in stability of the user's masticatory system, or may take comfort that results of a previously performed procedure are not likely to be negated due to subsequent changes in the user's masticatory system. However, if the second impression record 30 does not match the first impression record 30, then the user's masticatory system has not remained stable. Oral appliance 10 may then be re-balanced in the manner described above and a third impression record 30 created. The user may be asked to return after some period of time, several weeks for example, so that the re-balancing of oral appliance 10 can be verified. A fourth impression record 30 is created and compared with the third impression record 30. If the fourth impression record 30 matches the third impression record 30, then the user's masticatory system may be determined to be stable. If not, then further re-balancing and subsequent monitoring may be performed until it is determined that the user's masticatory system is stable. These steps can be performed any number of times according to particular needs.

Particular embodiments of the present invention may provide one or more technical advantages. For example, in particular embodiments, an oral appliance is provided with upper and lower arches that may be constructed and "balanced" such that a first arch contacts a second arch only at three bearing points, and such that the first arch contacts these bearing points at substantially the same time, when the user bites down and the user's temporomandibular joint is in its proper natural position. When the oral appliance is in use, the three bearing point may be permitted to move substantially freely within corresponding substantially planar regions. However, in particular embodiments, due to the natural movement of the user's lower jaw about the joint, only the anterior bearing point remains in contact with its corresponding substantially planar region when the user is not biting down and the lower jaw is retracted. In particular embodiments, the anterior bearing point is formed such that it remains in contact with its corresponding substantially planar region regardless of positioning or movement of the lower jaw. Because it ensures that the joint is in its proper natural position when the user bites down, particular embodiments may not only reduce or eliminate the symptoms of grinding of the teeth (e.g., excessive wear of the teeth), but may further address and remediate the underlying physiological cause—improper positioning of the joint and associated musculature.

In particular embodiments, the present invention may eliminate the difficult and time-consuming task of constructing an oral appliance such that: (1) where two arches are provided, a significant portion of the surface of the upper (or lower) arch substantially simultaneously contacts a significant portion of the opposing surface of the lower (or upper) arch, or (2) where a single arch is provided, the surface of the upper (or lower) arch substantially simultaneously contacts all or most of the user's opposing lower (or upper) teeth. The use of posterior bearing points in addition to an anterior bearing point may reduce the amount of force transferred to the joint when the user bites down to approximately five percent of the force applied, which may be approximately the same as if the entire surfaces of first and second arches contacted each other at the same time. Thus, in particular embodiments, the present invention may provide the same or similar advantages as such an arrangement, while reducing the complexity and time involved in construction. In addition, the use of bearing points and corresponding substantially planar regions may allow the first and second arches to be thinner and more comfortable to wear.

In particular embodiments, a dentist or other clinical professional may monitor the stability of the user's temporomandibular joint, associated musculature, teeth, or one or more other aspects of the user's masticatory system over time according to a series of impression records created using the oral appliance. For example, if the monitoring indicates that the joint has remained sufficiently stable over a period of time between the creation of successive impression records, then the dentist or other clinical professional may be comfortable finalizing the user's case. If not, then the dentist or clinical professional may wish to modify the oral appliance, such as by modifying one or more of the bearing points, to attempt to achieve such stability. In particular embodiments, monitoring may be conducted in connection with the initial fitting and construction of the oral appliance, such as over a period of less than one hour. In particular embodiments, monitoring may be conducted over a longer period, such as over a period of between one week and one year. In particular embodiments, such monitoring may allow a dentist or other clinical professional to make more effective treatment decisions and more accurately predict the likely effects of those decisions.

FIG. 6 illustrates an example method of constructing an oral appliance for maintaining stability of one or more aspects of a user's masticatory system. In a particular embodiment, the method includes at step 100 forming a first arch 12, 14 including anterior, right posterior, and left posterior substantially planar regions 22, 24, 26. At step 102, a second arch 14, 12 is formed including anterior, right posterior, and left posterior bearing points 16, 18, 20, each bearing point 16, 18, 20 of second arch 14, 12 being operable to contact and move substantially freely within the corresponding substantially planar region 22, 24, 25 of first arch 12, 14. The method may further include, at step 104, balancing oral appliance 10 such that first arch 12, 14 contacts second arch 14, 12 only at bearing points 16, 18, 20 and also that first arch 12, 14 contacts bearing points 16, 18, 20 at substantially the same time when the user bites down and the user's temporomandibular joint is in its proper natural position.

FIG. 7 illustrates an example method of monitoring stability of one or more aspects of a user's masticatory system using an oral appliance. In a particular embodiment, the method includes at step 200 providing oral appliance 10 including a first arch 12, 14 and a second arch 14, 12, the first arch 12, 14 operable to contact the second arch 14, 12 at only three bearing points 16, 18, 20 when the user bites down with oral appliance 10 inserted in the user's mouth and the user's temporomandibular joint in its proper natural position. Oral appliance 10 is inserted into the user's mouth at step 202, the dentist or other clinical professional places the joint in its proper natural position at step 204, and an impression material is introduced between first arch 12, 14 and second arch 14, 12 at step 206. At step 208, a first impression record 30 is created using the impression material, indicating that first arch 12, 14 is able to contact second arch 14, 12 at only the three bearing points 16, 18, 20 when the user bites down with oral appliance 10 inserted in the user's mouth and the joint in its proper natural position.

Oral appliance 10 is again inserted into the user's mouth at step 210, the user's joint is again placed in its proper natural position at step 212, and an impression material is again introduced between first arch 12, 14 and second arch 14, 12 at step 214. At step 216, a subsequent impression record 30 is created using the impression material, indicating whether first arch 12, 14 is able to contact second arch 14, 12 at only the three bearing points 16, 18, 20 when the user bites down with oral appliance 10 inserted in the user's mouth and the joint in its proper natural position. At step 218, the subsequent impression record 30 is compared to the previous impression record 30. If the subsequent impression record 30 matches the previous impression record 30 at step 220, then at step 222 it is determined that at least one or more aspects, if not all, of the user's masticatory system has remained stable over a period of time between creation of the previous and subsequent impression records 30. At step 224 a treatment decision is made according to the determination.

Alternatively, if the subsequent impression record 30 does not match the previous impression record 30 at step 220, then at step 226 it is determined that the user's masticatory system has not remained stable over the period of time between creation of the previous and subsequent impression records 30. In this case, at step 228, one or more modifications to oral appliance 10 are made, such that first arch 12, 14 is able to contact second arch 14, 12 at only the three bearing points 16, 18, 20 when the user bites down with oral appliance 10 inserted in the user's mouth and the joint in its proper natural position. The method returns to step 210 for creation of another subsequent impression record 30. The method may iterate in this manner until a subsequent impression record 30 matches a previous impression record 30 at step 220. The method may be conducted in connection with the initial fitting and construction of oral appliance 10, such as over a period of less than one hour for example. In addition or alternatively, the method may be conducted to determine long term stability of one or more aspects of the user's masticatory system, such as over a period of between one week and one year for example.

Although the present invention has been described above in connection with several embodiments, a plethora of changes, substitutions, variations, alterations, transformations, and modifications may be suggested to one skilled in the art, and it is intended that the present invention encompass such changes, substitutions, variations, alterations, transformations, and modifications as fall within the spirit and scope of the appended claims.

What is claimed is:

1. An oral appliance for maintaining long-term stability of one or more aspects of a user's masticatory system over an extended therapeutic period spanning numerous uses of the oral appliance, comprising:

a first arch adapted to receive at least some of a user's teeth, the first arch comprising an anterior substantially planar region located substantially proximate a center of the first arch, region a right posterior substantially planar region, and a left posterior substantially planar region; and a second arch adapted to receive at least some of the user's teeth, the second arch comprising an anterior bearing point located substantially proximate a center of the second arch, a right posterior bearing point, and a left posterior bearing point, the second arch operable to remain uncoupled from the first arch when the user bites down with the oral appliance inserted in the user's mouth during each of the numerous uses over the extended therapeutic period, each bearing point of the second arch operable to contact and apply a force substantially vertically against an exposed exterior substantially horizontal occlusal surface of a corresponding substantially planar region of the first arch when the user bites down with the oral appliance inserted in the user's mouth and the users temporomandibular joint in its proper natural position during each of the numerous uses over the extended therapeutic period;

the bearing points and corresponding substantially planar regions collectively adapted to maintain long-term stability of one or more aspects of the user's masticatory system over the extended therapeutic period spanning the numerous uses of the oral appliance.

2. The oral appliance of claim 1, wherein the first arch is an upper arch and the second arch is a lower arch.

3. The oral appliance of claim 1, wherein the first and second arches comprise custom arches customized to fit the user's dentition.

4. The oral appliance of claim 1, wherein:

the anterior substantially planar region and corresponding anterior bearing point are located in proximity to the user's most anterior teeth; and the posterior substantially planar regions and corresponding posterior bearing points are located in proximity to the user's most posterior teeth.

5. The oral appliance of claim 1, wherein at least the anterior bearing point of the second arch is operable to move substantially freely in contact with the exposed exterior substantially horizontal occlusal surface of the corresponding substantially planar region of the first arch when the oral appliance is inserted in the user's mouth.

6. The oral appliance of claim 1, wherein the anterior bearing point is constructed such that when oral appliance is inserted in the user's mouth the anterior bearing point remains in contact with and applies a force substantially vertically against the exposed exterior substantially horizontal occlusal surface of the corresponding substantially planar region regardless of positioning or movement of the lower jaw.

7. The oral appliance of claim 1, wherein the oral appliance is adapted to help maintain proper positioning of the user's temporomandibular joint over the extended therapeutic period spanning the numerous uses of the oral appliance.

8. A method of constructing an oral appliance for maintaining long-term stability of one or more aspects of a user's masticatory system over an extended therapeutic period spanning numerous uses of the oral appliance, comprising:

forming a first arch adapted to receive at least some of a user's teeth, the first arch comprising an anterior substantially planar region located substantially proximate a center of the first arch, a right posterior substantially planar region, and a left posterior substantially planar region; and forming a second arch adapted to receive at least some of the user's teeth, the second arch comprising an anterior bearing point located substantially proximate a center of the second arch, a right posterior bearing point, and a left posterior bearing point, the second arch operable to remain uncoupled from the first arch when the user bites down with the oral appliance inserted in the user's mouth during each of the numerous uses over the extended therapeutic period, each bearing point of the second arch operable to contact and apply a force substantially vertically against an exposed exterior substantially horizontal occlusal surface of a corresponding substantially planar region of the first arch when the user bites down with the oral appliance inserted in the user's mouth and the users temporomandibular joint in its proper natural position during each of the numerous uses over the extended therapeutic period;

the bearing points and corresponding substantially planar regions collectively adapted to maintain long-term stability of one or more aspects of the user's masticatory system over the extended therapeutic period spanning the numerous uses of the oral appliance;

the constructed oral appliance comprising the first and second arches.

9. The method of claim 8, wherein the first arch is an upper arch and the second arch is a lower arch.

10. The method of claim 8, wherein the first and second arches comprise custom arches customized to fit the user's dentition.

11. The method of claim 8, wherein:

the anterior substantially planar region and corresponding anterior bearing point are located in proximity to the user's most anterior teeth; and the posterior substantially planar regions and corresponding posterior bearing points are located in proximity to the user's most posterior teeth.

12. The method of claim 8, wherein at least the anterior bearing point of the second arch is operable to move substantially freely in contact with the exposed exterior substantially horizontal occlusal surface of the corresponding substantially planar region of the first arch when the oral appliance is inserted in the user's mouth.

13. The method of claim 8, wherein the anterior bearing point is formed such that when oral appliance is inserted in the user's mouth the anterior bearing point remains in contact with and applies a force substantially vertically against the exposed exterior substantially horizontal occlusal surface of the corresponding substantially planar region regardless of positioning or movement of the lower jaw.

14. The method of claim 8, wherein the oral appliance is adapted to help maintain proper positioning of the user's temporomandibular joint over the extended therapeutic period spanning the numerous uses of the oral appliance.

15. A method of monitoring positioning of a user's temporomandibular joint, comprising:

providing an oral appliance comprising a first arch and a second arch each adapted to receive at least some of the user's teeth, the first arch operable to contact the second arch at only three bearing points when the user bites down with the oral appliance inserted in the user's mouth and the user's temporomandibular joint in its proper natural position;

inserting the oral appliance into the user's mouth;

introducing an impression material between the first and second arches;

creating a first impression record using the impression material, indicating that the first arch is operable to contact the second arch at only the three bearing points when the user bites down with the oral appliance inserted in the user's mouth and the user's temporomandibular joint in its proper natural position;

again inserting the oral appliance into the user's mouth;

again introducing an impression material between the first and second arches;

creating a second impression record using the impression material, indicating whether the first arch is operable to contact the second arch at only the three bearing points when the user bites down with the oral appliance inserted in the user's mouth and the user's temporomandibular joint in its proper natural position;

comparing the second impression record to the first impression record; and if the second impression record matches the first impression record, then determining that one or more aspects of the user's masticatory system have remained stable over a period of time between creation of the first and second impression records.

16. The method of claim 15, wherein the first arch is an upper arch and the second arch is a lower arch.

17. The method of claim 15, wherein the first and second arches comprise custom arches customized to fit the user's dentition.

18. The method of claim 15, wherein the three bearing points comprise an anterior bearing point, a right posterior bearing point, and a left posterior bearing point.

19. The method of claim 18, wherein:
the first arch comprises an anterior substantially planar region, right posterior substantially planar region, and left posterior substantially planar region; and
the second arch comprises the anterior bearing point, right posterior bearing point, and left posterior bearing point, at least the anterior bearing point of the second arch being operable to contact and move substantially freely within a corresponding substantially planar region of the first arch.

20. The method of claim 19, wherein:
the anterior substantially planar region and corresponding anterior bearing point are located in proximity to the user's most anterior teeth; and
the posterior substantially planar regions and corresponding posterior bearing points are located in proximity to the user's most posterior teeth.

21. The method of claim 15, wherein the impression material comprises a BLU-MOUSSE material.

22. The method of claim 15, further comprising, if the second impression record does not match the first impression record:
determining that one or more aspects of the user's masticatory system have not remained stable over the period of time between creation of the first and second impression records; and
modifying one or more of the bearing points such that the first arch is operable to contact the second arch at only the three bearing points when the user bites down with the oral appliance inserted in the user's mouth and the user's temporomandibular joint in its proper natural position.

23. The method of claim 15, wherein the period of time is between zero and sixty minutes and the monitoring is performed in connection with initial fitting of the oral appliance for the user.

24. The method of claim 15, wherein the period of time is between one week and fifty-two weeks and the monitoring is performed to determine long term stability of the user's masticatory system.

25. The method of claim 15, wherein the oral appliance is operable to help maintain stability of one or more aspects of the user's masticatory system, at least helping to maintain proper positioning of the user's temporomandibular joint.

26. A method of maintaining long-term stability of one or more aspects of a user's masticatory system over an extended therapeutic period spanning numerous uses of an oral appliance, comprising:
providing to the user, for use in maintaining long-term stability of one or more aspects of the user's masticatory system over the extended therapeutic period, a first arch of the oral appliance adapted to receive at least some of the user's teeth, the first arch comprising an anterior substantially planar region located substantially proximate a center of the first arch, a right posterior substantially planar region, and a left posterior substantially planar region; and
providing to the user, for use in maintaining long-term stability of one or more aspects of the user's masticatory system over the extended therapeutic period, a second arch of the oral appliance adapted to receive at least some of the user's teeth, the second arch comprising an anterior bearing point located substantially proximate a center of the second arch, a right posterior bearing point, and a left bearing point, the second arch operable to remain uncoupled from the first arch when the user bites down with the oral appliance inserted in the user's mouth during each of the numerous uses over the extended therapeutic period, each bearing point of the second arch operable to contact and apply a force substantially vertically against an exposed exterior substantially horizontal occlusal surface of a corresponding substantially planar region of the first arch when the user bites down with the oral appliance inserted in the user's mouth and the user's temporomandibular joint in its proper natural position during each of the numerous uses over the extended therapeutic period;
the bearing points and corresponding substantially planar regions collectively adapted to maintain long-term stability of one or more aspects of the user's masticatory system over the extended therapeutic period spanning the numerous uses of the oral appliance.

27. The method of claim 26, wherein the first arch is an upper arch and the second arch is a lower arch.

28. The method of claim 26, wherein the first and second arches comprise custom arches customized to fit the user's dentition.

29. The method of claim 26, wherein:
the anterior substantially planar region and corresponding anterior bearing point are located in proximity to the user's most anterior teeth; and
the posterior substantially planar regions and corresponding posterior bearing points are located in proximity to the user's most posterior teeth.

30. The method of claim 26, wherein at least the anterior bearing point of the second arch is operable to move substantially freely in contact with the exposed exterior substantially horizontal occlusal surface of the corresponding substantially planar region of the first arch when the oral appliance is inserted in the user's mouth.

31. The method of claim 26, wherein the anterior bearing point is formed such that when the oral appliance is inserted in the user's mouth the anterior bearing point remains in contact with and applies a force substantially vertically against the exposed exterior substantially horizontal occlusal surface of the corresponding substantially planar region regardless of positioning or movement of the lower jaw.

32. The method of claim 26, wherein the oral appliance is adapted to help maintain proper positioning of the user's temporomandibular joint over the extended therapeutic period spanning the numerous uses of the oral appliance.

33. A method of maintaining long-term stability of one or more aspects of a user's masticatory system over an extended therapeutic period spanning numerous uses of an oral appliance, comprising:

during each of the numerous uses over the extended therapeutic period, for purposes of maintaining long-term stability of one or more aspects fo the user's masticatory system, inserting into the user's mouth a first arch of the oral appliance adapted to receive at least some of the user's teeth, the first arch comprising an anterior substantially planar region located substantially proximate a center of the first arch, a right posterior substantially planar region, and a left posterior substantially planar region; and during each of the numerous uses over the extended therapeutic period, for purposes of maintaining long-term stability of one or more aspects of the user's masticatory system, inserting into the user's mouth a second arch of the oral appliance adapted to receive at least some of the user's teeth, the second arch comprising an anterior bearing point located substantially proximate a center of the second arch, a right posterior bearing point, and a left posterior bearing point, the second arch operable to remain uncoupled from the first arch when the user bites down with the oral appliance inserted in the user's mouth during each of the numerous uses over the extended therapeutic period, each bearing point of the second arch operable to contact and apply a force substantially vertically against an exposed exterior substantially horizontal occlusal surface of a corresponding substantially planar region of the first arch when the user bites down with the oral appliance inserted in the user's mouth and the user's temporomandibular joint in its proper natural position during each of the numerous uses over the extended therapeutic period;

the bearing points and corresponding substantially planar regions collectively adapted to maintain long-term stability of one or more aspects of the user's masticatory system over the extended therapeutic period spanning the numerous uses of the oral appliance.

34. The method of claim 33, wherein the first arch is an upper arch and the second arch is a lower arch.

35. The method of claim 33, wherein the first and second arches comprise custom arches customized to fit the user's dentition.

36. The method of claim 33, wherein:
the anterior substantially planar region and corresponding anterior bearing point are located in proximity to the user's most anterior teeth; and
the posterior substantially planar regions and corresponding posterior bearing points are located in proximity to the user's most posterior teeth.

37. The method of claim 33, wherein at least the anterior bearing point of the second arch is operable to move substantially freely in contact with the exposed exterior substantially horizontal occlusal surface of the corresponding substantially planar region of the first arch when the oral appliance is inserted in the user's mouth.

38. The method of claim 33, wherein the anterior bearing point is formed such that when the oral appliance is inserted in the user's mouth the anterior bearing point remains in contact with and applies a force substantially vertically against the exposed exterior substantially horizontal occlusal surface of the corresponding substantially planar region regardless of positioning or movement of the lower jaw.

39. The method of claim 33, wherein the oral appliance is adapted to help maintain proper positioning of the user's temporomandibular joint over the extended therapeutic period spanning the numerous uses of the oral appliance.

* * * * *